United States Patent
Struble et al.

(10) Patent No.: US 8,391,978 B2
(45) Date of Patent: Mar. 5, 2013

(54) METHOD AND APPARATUS FOR ADJUSTING SENSITIVITY USING INTRACARDIAC PRESSURE DATA

(75) Inventors: Chester L. Struble, Eijsden (NL); Pierre A. Grandjean, Warsage (BE)

(73) Assignee: Medtronic, Inc., Minneapolis, MN (US)

( * ) Notice: Subject to any disclaimer, the term of this patent is extended or adjusted under 35 U.S.C. 154(b) by 1679 days.

(21) Appl. No.: 11/380,353

(22) Filed: Apr. 26, 2006

(65) Prior Publication Data

US 2007/0255151 A1    Nov. 1, 2007

(51) Int. Cl.
*A61N 1/365*    (2006.01)
(52) U.S. Cl. .............. 607/18; 607/23; 607/25; 607/28
(58) Field of Classification Search .............. 600/513; 607/9, 18, 23
See application file for complete search history.

(56) References Cited

U.S. PATENT DOCUMENTS

| | | | |
|---|---|---|---|
| 5,330,505 A | 7/1994 | Cohen | |
| 5,374,282 A * | 12/1994 | Nichols et al. | 607/18 |
| 5,626,623 A | 5/1997 | Kieval et al. | |
| 5,882,352 A * | 3/1999 | Duncan et al. | 607/4 |
| 6,772,009 B2 | 8/2004 | Zhang et al. | |
| 6,871,088 B2 | 3/2005 | Chinchoy | |
| 6,882,882 B2 | 4/2005 | Struble et al. | |
| 7,136,705 B1 * | 11/2006 | Park | 607/27 |
| 2004/0049235 A1 | 3/2004 | Deno et al. | |
| 2004/0172081 A1 | 9/2004 | Wang | |
| 2005/0288725 A1 | 12/2005 | Hettrick et al. | |

OTHER PUBLICATIONS

International Search Report, PCT/US2007/064591, Nov. 28, 2007, 7 pages.

\* cited by examiner

*Primary Examiner* — Carl H Layno
*Assistant Examiner* — Allen Porter, Jr.
(74) *Attorney, Agent, or Firm* — Reed A. Duthler; Stephen W. Bauer (57) ABSTRACT

A method and apparatus for adjusting the electrogram (EGM) sensitivity level of an implantable medical device using intracardiac pressure data. An EGM is monitored to detect electrical events and intracardiac pressure is monitored to detect pressure waves. The electrical waves and pressure waves are analyzed to determine the presence of a one-to-one correlation, with the absence of a one-to-one correlation indicating the need to adjust the sensitivity level.

10 Claims, 6 Drawing Sheets

METHOD AND APPARATUS FOR ADJUSTING SENSITIVITY USING INTRACARDIAC PRESSURE DATA

BACKGROUND

Implantable medical devices (IMDS) which monitor cardiac signals are commonly used in monitoring and treating patients. For example, pacemakers can monitor cardiac activity and can also provide electrical stimulation to the heart. Some pacemakers stimulate the heart at regular intervals and others sense cardiac electrical activity and deliver electrical stimuli to the heart intermittently as needed. Therefore the ability to accurately detect and interpret cardiac electrical signals is important to cardiac monitoring and to the delivery of proper pacemaker therapy.

The ability of an IMD to sense cardiac electrical signals is typically controllable by means of circuitry for adjusting the sensitivity threshold of the pacemaker's sense amplifier, such that electrical signals resulting from depolarization of the cardiac muscle must exceed this sensitivity threshold in order for the cardiac event to be recognized. The sensitivity threshold may be defined in terms of a minimum voltage level for the input signal, or a minimum time period during which the input signal must exceed a minimum voltage level. The sensitivity threshold may be preset during manufacture or may be programmed by the physician at the time of implantation.

The sense amplifier circuitry of the IMD must be sensitive enough to ensure detection of cardiac signals, which are typically of relatively low magnitude, especially in the case of atrial sensing. However, the sense amplifier must not be so sensitive that certain non-electrical cardiac signals, such as electromagnetic noise, myopotentials, and the like, cause the IMD to erroneously sense a cardiac signal which did not actually occur. For example, in the case of pacemakers, if the sense amplifier circuitry is not sensitive enough (undersensing), the pacemaker could lose synchronization with the natural cardiac rhythm or deliver pacing stimuli at inappropriate times. However, if the sense amplifier circuitry sensitivity is set too low (oversensing), the pacemaker could erroneously sense a cardiac signal which did not occur.

The strength of cardiac signals received at the sense amplifiers inputs may change over time. Thus, a sensitivity threshold that is appropriate for a patient at the time of implantation might, at some later time, prove to be too high or too low, leading to undersensing or oversensing. Changes in the strength of the electrical cardiac signals received by the IMD may result from normal or pathological changes in the heart's intrinsic activity, from lead maturation effects such as changes in the positioning of implanted leads, or changes in the conductive properties of the heart muscle in the region surrounding the leads, such as might result from myocardial infarction and fibrotic tissue growth around the lead. Thus it is desirable for IMDs such as pacemakers to have an adjustable sensitivity threshold with the ability to determine an optimal sensitivity level.

DETAILED DESCRIPTION

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims.

Embodiments of the invention include implantable medical devices capable of sensing both cardiac electrical signals and intracardiac pressure. By comparing cardiac electrical signals to intracardiac pressure data, the implantable medical device can detect the presence of oversensing or undersensing of electrical signals and can identify the need for sensitivity adjustment. The IMD can also use this comparison to identify an optimal sensitivity. Certain embodiments of the invention may include, or may be adapted for use in, diagnostic monitoring equipment, external medical device systems, and IMDs, including implantable hemodynamic monitors (IHMs), implantable cardioverter-defibrillators (ICDs), cardiac pacemakers, cardiac resynchronization therapy (CRT) pacing devices, drug delivery devices, or combinations of such devices.

Figure 1:
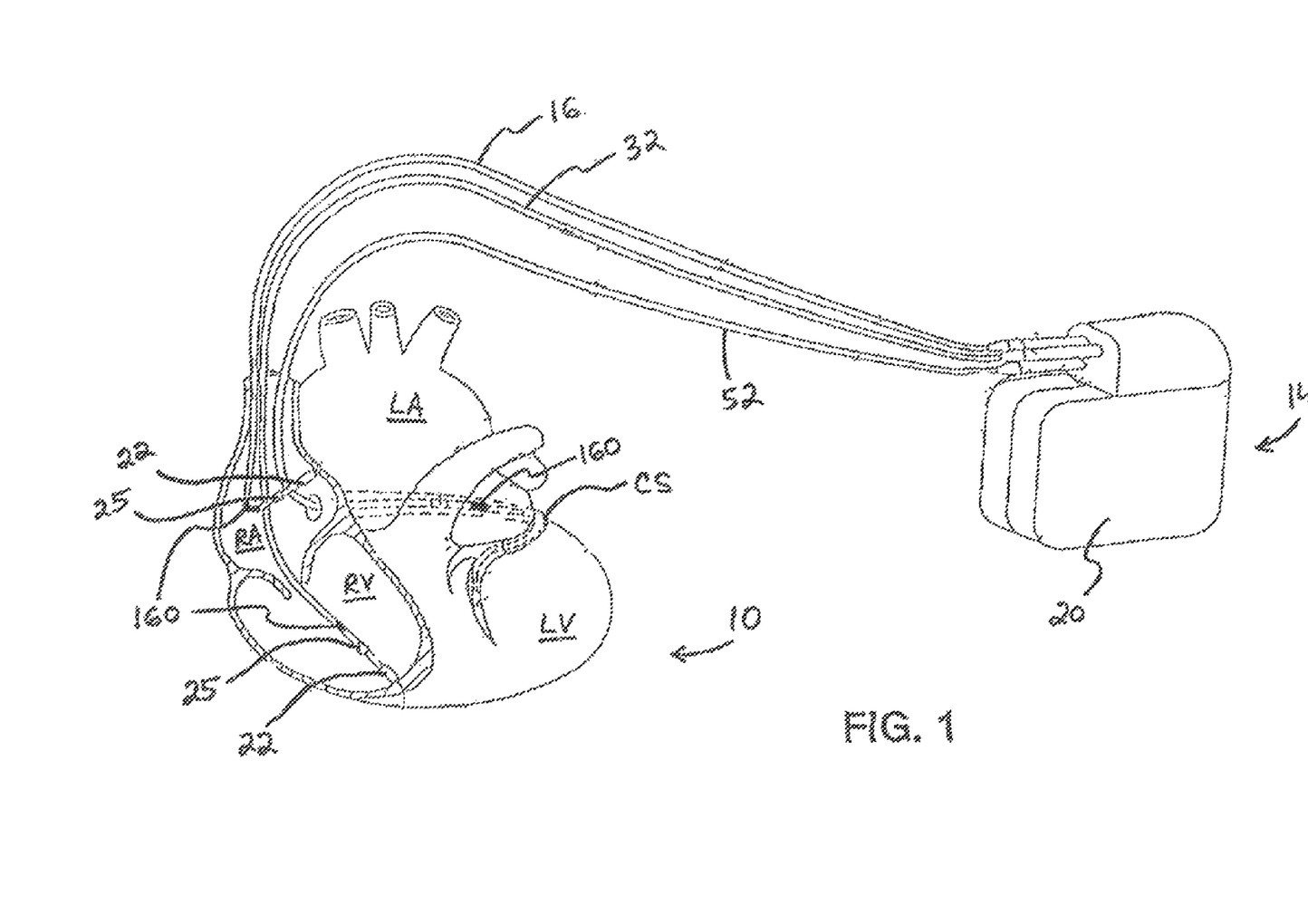
FIG. 1 is a schematic diagram depicting a multi-channel, atrial and bi-ventricular, monitoring/pacing IMD in which embodiments of the invention may be implemented.

FIG. 1 is a schematic representation of an IMD 14 that may be used in accordance with certain embodiments of the invention. The IMD 14 may be any device that is capable of measuring hemodynamic parameters (e.g., blood pressure signals) from within a chamber of a patient's heart, and which may further be capable of measuring other signals, such as the patient's EGM.

In FIG. 1, heart 10 includes the right atrium (RA), left atrium (LA), right ventricle (RV), left ventricle (LV), and the coronary sinus (CS) extending from the opening in the right atrium laterally around the atria to form the great vein and branches thereof.

FIG. 1 depicts IMD 14 in relation to heart 10. In certain embodiments, IMD 14 may be an implantable, multi-channel cardiac pacemaker that may be used for restoring AV synchronous contractions of the atrial and ventricular chambers and simultaneous or sequential pacing of the right and left ventricles. Three endocardial leads 16, 32 and 52 connect the IMD 14 with the RA, the RV and the LV, respectively. Each lead has at least one electrical conductor and pace/sense electrode, and a can electrode 20 may be formed as part of the outer surface of the housing of the IMD 14. The pace/sense electrodes, e.g. 22 and 25, and can electrode 20 may be selectively employed to provide a number of unipolar and bipolar pace/sense electrode combinations for pacing and sensing functions. The depicted positions in or about the right and left heart chambers are merely exemplary. Moreover other leads and pace/sense electrodes may be used instead of the depicted leads and pace/sense electrodes.

Typically, in pacing systems of the type illustrated in FIG. 1, the electrodes designated above as "pace/sense" electrodes are used for both pacing and sensing, functions. In accordance with one aspect of the present invention, these "pace/sense" electrodes, e.g. 22 and 25, can be selected to be used exclusively as pace or sense electrodes or to be used in common as pace/sense electrodes in programmed combinations for sensing cardiac signals and delivering pace pulses along pacing and sensing vectors.

In addition, some or all of the leads shown in FIG. 1 could carry one or more pressure sensors 160 for measuring systolic and diastolic pressures, and a series of spaced apart impedance sensing leads for deriving volumetric measurements of the expansion and contraction of the RA, LA, RV and LV.

The leads and circuitry described above can be employed to record EGM signals, blood pressure signals, and impedance values over certain time intervals. The recorded data may be periodically telemetered out to a programmer operated by a physician or other healthcare worker in an uplink telemetry transmission during a telemetry session, for example.

Figure 2:
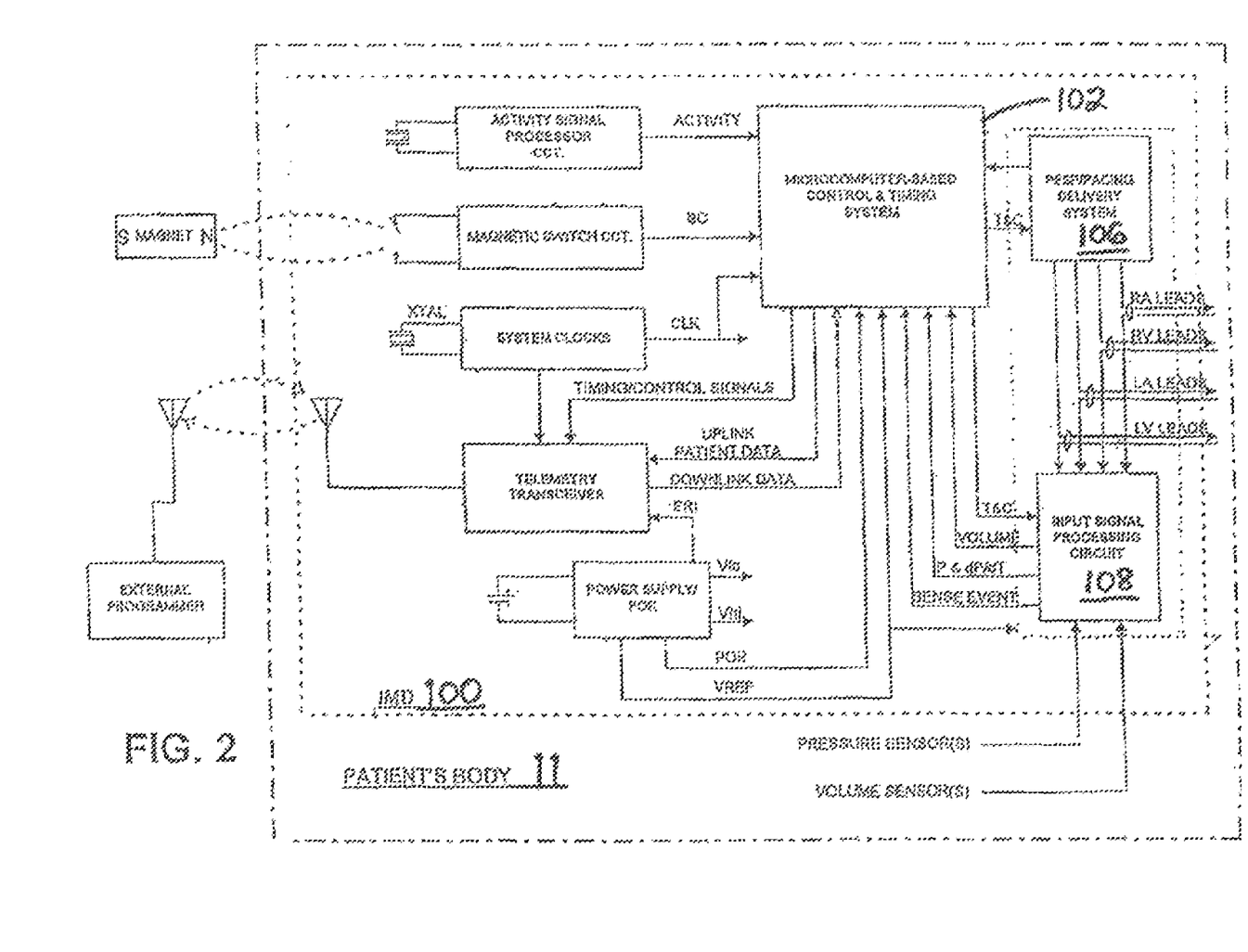
FIG. 2 is a simplified block diagram of an embodiment of IMD circuitry and associated leads that may be employed in the system of FIG. 1 to enable selective therapy delivery and monitoring in one or more heart chamber.

FIG. 2 depicts a system architecture of an exemplary multi-chamber monitor/sensor 100 implanted into a patient's body 11 that provides delivery of a therapy and/or physiologic input signal processing. The typical multi-chamber monitor/sensor 100 has a system architecture that is constructed about a microcomputer-based control and timing system 102 which varies in sophistication and complexity depending upon the type and functional features incorporated therein. The functions of microcomputer-based multi-chamber monitor/sensor control and timing system 102 are controlled by firmware and programmed software algorithms stored in RAM and ROM including PROM and EEPROM and are carried out using a CPU or ALU of a typical microprocessor core architecture.

The therapy delivery system 106 can be configured to include circuitry for delivering cardioversion/defibrillation shocks and/or cardiac pacing pulses delivered to the heart or cardiomyostimulation to a skeletal muscle wrapped about the heart. Alternately, the therapy delivery system 106 can be configured as a drug pump for delivering drugs into the heart to alleviate heart failure or to operate an implantable heart assist device or pump implanted in patients awaiting a heart transplant operation.

The input signal processing circuit 108 includes at least one physiologic sensor signal processing channel for sensing and processing a sensor derived signal from a physiologic sensor located in relation to a heart chamber or elsewhere in the body. Examples illustrated in FIG. 2 include pressure and volume sensors, but could include other physiologic or hemodynamic sensors.

Figure 3:
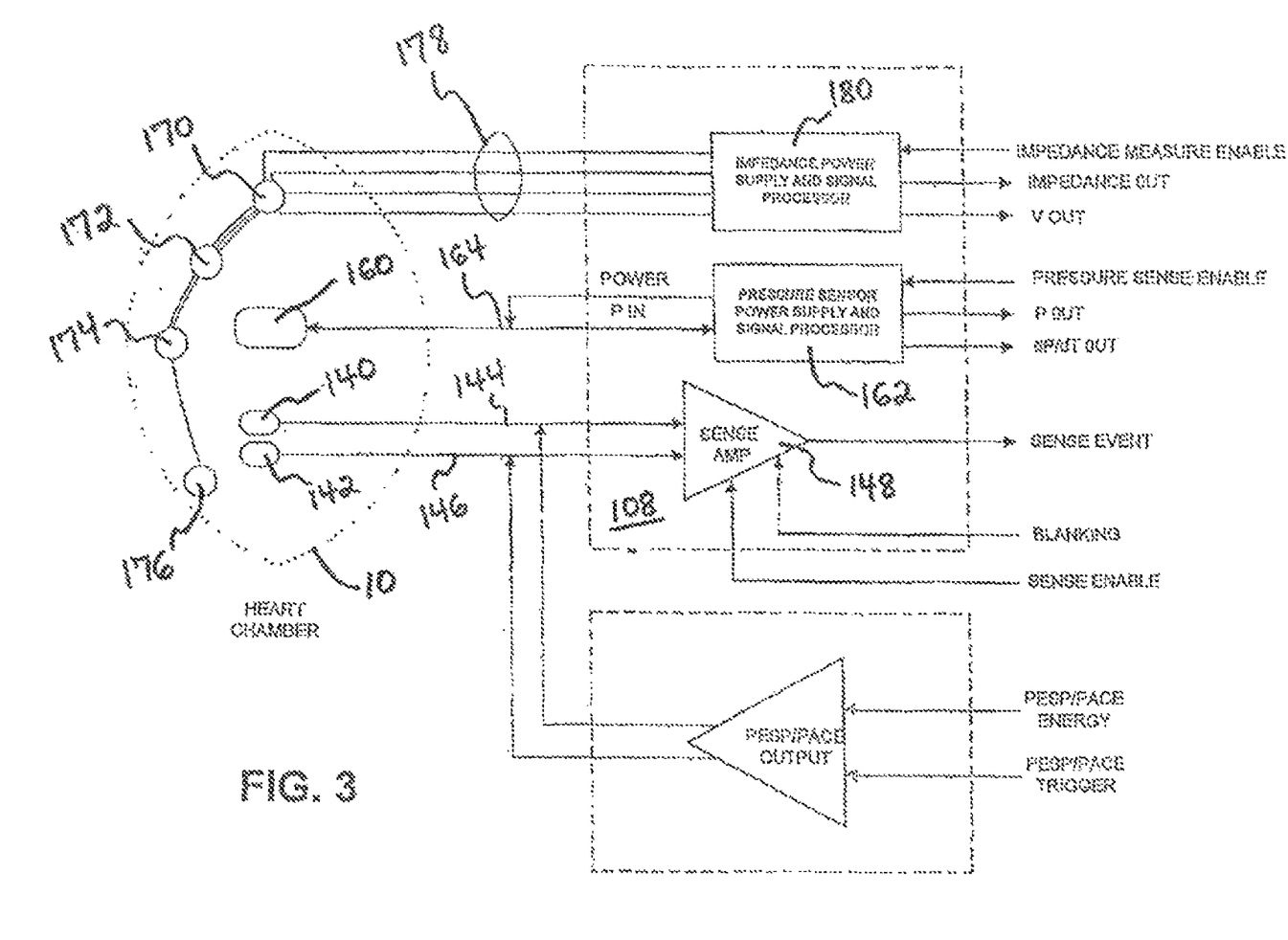
FIG. 3 is a simplified block diagram of a single monitoring and pacing channel for acquiring pressure, impedance and cardiac electrogram (EGM) signals employed in monitoring cardiac function and/or delivering therapy, including pacing therapy, in accordance with embodiments of the invention.

FIG. 3 schematically illustrates one pacing, sensing and parameter measuring channel in relation to one heart chamber. A pair of pace/sense electrodes 140, 142, a pressure sensor 160, and a plurality, e.g., four, impedance measuring electrodes 170, 172, 174, 176 are located in operative relation to the heart 10.

The pair of pace/sense electrodes 140, 142 are located in operative relation to the heart 10 and coupled through lead conductors 144 and 146, respectively, to the inputs of a sense amplifier 148 located within the input signal processing circuit 108. The sense amplifier 148 is selectively enabled by the presence of a sense enable signal that is provided by control and timing system 102. The sense amplifier 148 is enabled during prescribed times when pacing is either enabled or not enabled in a manner known in the pacing art. The blanking signal is provided by control and timing system 102 upon delivery of a pacing or PESP pulse or pulse train to disconnect the sense amplifier inputs from the lead conductors 144 and 146 for a short blanking period in a manner well known in the art. The sense amplifier provides a sense event signal signifying the contraction of the heart chamber commencing a heart cycle based upon characteristics of the EGM. The control and timing system responds to non-refractory sense events by restarting an escape interval (EI) timer timing out the EI for the heart chamber, in a manner well known in the pacing art.

The pressure sensor 160 is coupled to a pressure sensor power supply and signal processor 162 within the input signal processing circuit 108 through a set of lead conductors 164. Lead conductors 164 convey power to the pressure sensor 160, and convey sampled blood pressure signals from the pressure sensor 160 to the pressure sensor power supply and signal processor 162. The pressure sensor power supply and signal processor 162 samples the blood pressure impinging upon a transducer surface of the sensor 160 located within the heart chamber when enabled by a pressure sense enable signal from the control and timing system 102. Absolute pressure (P), developed pressure (DP) and pressure rate of change (dP/dt) sample values can be developed by the pressure sensor power supply and signal processor 162 or by the control and timing system 102 for storage and processing.

A variety of hemodynamic parameters may be recorded, for example, including right ventricular (RV) systolic and diastolic pressures (RVSP and RVDP), estimated pulmonary artery diastolic pressure (ePAD), pressure changes with respect to time (dP/dt), heart rate, activity, and temperature. Some parameters may be derived from others, rather than being directly measured. For example, the ePAD parameter may be derived from RV pressures at the moment of pulmonary valve opening, and heart rate may be derived from information in an intracardiac EGM recording.

The set of impedance electrodes 170, 172, 174 and 176 is coupled by a set of conductors 178 and is formed as a lead that is coupled to the impedance power supply and signal processor 180. Impedance-based measurements of cardiac parameters such as stroke volume are known in the art, such as an impedance lead having plural pairs of spaced surface electrodes located within the heart 10. The spaced apart electrodes can also be disposed along impedance leads lodged in cardiac vessels, e.g., the coronary sinus and great vein or attached to the epicardium around the heart chamber. The impedance lead may be combined with the pace/sense and/or pressure sensor bearing lead.

The data stored by IMD 14 may include continuous or intermittent monitoring of various parameters, for example recording intracardiac EGM data at sampling rates as fast as 256 Hz or faster. In certain embodiments of the invention, an IHM may alternately store summary forms of data that may allow storage of data representing longer periods of time. In one embodiment, hemodynamic pressure parameters may be summarized by storing a number of representative values that describe the hemodynamic parameter over a given storage interval. The mean, median, an upper percentile, and a lower percentile are examples of representative values that may be stored by an IHM to summarize data over an interval of time (e.g., the storage interval). In one embodiment of the invention, a storage interval may contain six minutes of data in a data buffer, which may be summarized by storing a median value, a 94th percentile value (i.e., the upper percentile), and a 6th percentile value (i.e., the lower percentile) for each hemodynamic pressure parameter being monitored. In this manner, the memory of the IHM may be able to provide weekly or monthly (or longer) views of the data stored. The data buffer, for example, may acquire data sampled at a 256

Hz sampling rate over a 6 minute storage interval, and the data buffer may be cleared out after the median, upper percentile, and lower percentile values during that 6 minute period are stored. It should be noted that certain parameters measured by the IHM may be summarized by storing fewer values, for example storing only a mean or median value of such parameters as heart rate, activity level, and temperature, according to certain embodiments of the invention.

Hemodynamic parameters that may be used in accordance with various embodiments of the invention include parameters that are directly measured, such as RVDP and RVSP, as well as parameters that may be derived from other pressure parameters, such as ePAD, dP/dt, etc.

In order to accurately monitor cardiac activity, the IMD must be able to discriminate between electrical activity that represents cardiac depolarization and electrical activity that is actually non-cardiac electrical noise. Thus the sensitivity threshold must be low enough to detect cardiac activity but high enough to filter out causes of EGM deflections. If the sensitivity is too high, such that the IMD does not detect cardiac activity, inappropriate therapy such as unnecessary cardiac pacing may be delivered. Similarly, if the sensitivity of the IMD is too low, such that background noise is detected by the IMD as cardiac electrical activity, the IMD may not detect the need for pacing when pacing is required or may inaccurately detect an abnormally elevated rhythm such as ventricular tachycardia and may deliver an unnecessary cardioversion shock.

The sensitivity of the IMD represents the threshold for detection of an electrical event using an EGM. Thus a high sensitivity corresponds to a low threshold value for detection and a low sensitivity corresponds to a high detection threshold value. For example, for the ventricles, a low sensitivity may be greater than approximately 5 mV and a high sensitivity may be less than approximately 1.5 mV. In the atria, in which electrical depolarizations produce smaller deflections of an EGM due to the smaller mass of the atria as compared to the ventricles, a low sensitivity may be greater than approximately 3 mV while a high sensitivity may be less than approximately 0.5 mV. Of course, these values are merely representative and depend on many different factors, including location of the sense electrodes.

Ideally, the sensitivity threshold of the IMD would allow it to detect all true electrical events and no non-cardiac electrical noise. While a given sensitivity may provide this ideal level of detection at a particular point in time, the optimal sensitivity level may change over time. Therefore, some embodiments of this invention monitor sensitivity and make necessary corrections intermittently and/or on a continuous basis.

The relationship between the EGM and the pressure signal may be monitored by the IMD to determine whether the sensitivity level is appropriate. The IMD detects an electrical event when the EGM exceeds a threshold, which is determined by the sensitivity level, as discussed above. Embodiments of this invention also monitor pressure data to detect a pressure wave at a particular point in time. The point in time at which a pressure wave occurs may be indicated by the dP/dt max, the maximum systolic pressure, or other detectable, periodic pressure values.

To determine whether an IMD is over or under sensing at a particular sensitivity setting, the detection of electrical events is compared to the detection of pressure waves. In the absence of over or under sensing, there should be a one-to-one relationship between detected electrical events and detected pressure waves, such that a detected pressure wave follows each electrical event, and there are no detected pressure waves without an associated detected electrical event.

The presence of a one-to-one relationship between detected electrical events and detected pressure waves may be determined in a variety of ways. For example, there may be a first window of time after each electrical event during which a pressure wave must occur in order for the events to be correlated. In addition or in the alternative, there may be a second backward looking window of time before each detected pressure wave during when an electrical event must be detected. For example, the windows may be between approximately 80 ms and 200 ms in the left ventricle, depending on factor such as heart rate, sensing electrode position, ventricular contractility, contraction patterns and the selected detection point on the pressure wave form. The first and second windows are measured from different starting points and may be of equal or unequal duration. If an electrical event is detected without a corresponding detected pressure wave within the first time window, the electrical event represents oversensing and sensitivity must be decreased (the value must be increased). Alternatively, if a pressure wave is detected without a corresponding electrical event within the second time window, the IMD is undersensing electrical activity and the sensitivity should be increased (the threshold should be lowered).

Alternatively, the IMD may allow a limited number of unassociated electrical events or pressure waves and may make adjustments to sensitivity only when the number of unassociated events occurs exceeds a limit. For example, the IMD may allow a certain number of unassociated electrical events or pressure waves per unit of time or at a certain frequency without making a sensitivity adjustment. In such embodiments, if the number of unassociated electrical events or pressure waves exceeds this limit, the sensitivity would be adjusted appropriately as noted above.

Alternatively, the presence of a one-to-one relationship between electrical events and pressure waves may be assessed by analyzing the time intervals between consecutive beats. Thus, the time interval from a first to a second electrical event is compared to the time interval from a first to a second pressure wave. If sensitivity is appropriate such that there is a one-to-one ratio between electrical events and pressure waves, the ratio of the electrical event time interval to the pressure wave time interval should be close to one. However, if the IMD is undersensing, one or more electrical events may not be detected, such that the time interval between consecutive electrical events will increase and the ratio of electrical event interval to pressure wave interval will be greater than one. For example, if a single electrical event is not detected, the time interval between electrical events will double and the ratio will be approximately two. Similarly, if oversensing occurs, additional electrical events will be detected, shortening the time interval between consecutive electrical events and producing a ratio of electrical event time intervals to pressure wave time intervals of less than one. A comparison between electrical event and pressure wave time intervals could be made on a beat to beat basis so that the intervals correspond appropriately. Other comparisons of the time intervals are also possible. For example, the electrical time interval could be subtracted from the pressure wave time interval, with a result close to zero expected when detection is appropriate.

Embodiments which detect oversensing or undersensing by monitoring for a one-to-one correlation between electrical events and pressure waves respond by increasing or decreasing sensitivity. For example, if an electrical event is detected without an associated pressure wave within the window at a sensitivity of 4 mV, oversensing is occurring and the IMD may decrease sensitivity to 5 mV. Alternatively, if a pressure wave is detected without an associated electrical wave at a sensitivity of 4 mV, undersensing is occurring and the IMD may increase sensitivity to 3 mV. The IMD would respond in the same way to oversensing or undersensing detected by monitoring for a one-to-one relationship between electrical events and pressure waves using the time intervals between consecutive beats described above. Following the sensitivity adjustment, monitoring for a one-to-one relationship between electrical events and pressure waves continues and further adjustments are made as necessary.

In addition to detecting oversensing and undersensing, the timing of the electrical event detection may be analyzed to detect marginal sensing. Marginal sensing occurs when there is no over or undersensing, but the sensitivity threshold is at the edge of the acceptable range and there is a risk that undersensing could occur. In some embodiments, the timing of electrical event detection is monitored by analyzing the time interval between an electrical event and a corresponding subsequently detected pressure wave, known as the electromechanical time. For example, the time interval may be determined for each beat. Thus, a time interval between a first electrical event and a first pressure wave is compared to the time interval between a second electrical event and a second pressure wave. If there is little variation in this interval from beat to beat, the sensitivity threshold is appropriate. However, if the interval varies from beat to beat, the sensitivity threshold may be marginal. This may occur, for example, when the sensitivity threshold is close to the peak amplitude of the electrical event. In such circumstances, there may be variation in the time at which the electrical event is detected from one beat to the next, resulting in variations in the timing of electrical event detection. Such variations may indicate that an increase in the sensitivity threshold may be appropriate.

Alternatively, variation in the timing of the detection of electrical events indicative of marginal sensing may be identified using the ratio of electrical event intervals to pressure wave intervals described above. With a marginal signal, sequential electrical event intervals may vary somewhat relative to the pressure wave intervals. The result is a ratio of electrical event intervals to pressure wave intervals which may be somewhat more or less than one with each consecutive beat. If the value of the ratio exceeds an allowable amount above or below one, this may indicate that the sensitivity is marginal and may need to be increased.

Slight variation in the timing of the detection of electrical events may occur even at optimal sensitivities levels. For example, at higher heart rates, the interval between an electrical event and a corresponding pressure wave may decrease. While heart rate may affect the length of this time interval, the timing variation will be small when neighboring beats are compared, as heart rate changes occur gradually over a series of beats. Therefore, this effect is minimized by analyzing the intervals on a beat to beat basis. Thus a small amount of beat to beat variation in the interval between the electrical event and pressure wave may not indicate that the sensitivity is marginal. For example, a variation of 5 ms may be allowable, while a variation of 30 ms may indicate that the sensitivity should be adjusted. Similarly, a small variation in the ratio of electrical event intervals to pressure wave intervals, such as ratios from 0.95 to 1.05 may be allowable while greater variation, such as ratios of less than 0.8 or greater than 1.2 may indicate the sensitivity is marginal and an adjustment may be required. Thus, timing variations of electrical event detection may only indicate marginal sensing when the variation exceeds an allowable limit, such as a predetermined amount.

For example, the IMD may detect a one-to-one relationship between electrical events and pressure waves as discussed above. However, the time interval between electrical events and pressure waves may vary from one beat to the next, such as by greater than 20 ms, indicating marginal sensing. Alternatively, marginal sensing may be identified by detecting ratios of the electrical event interval to pressure wave interval greater than 0.2 or less than 0.8. In these example, the IMD may determine that the sensitivity level is close to undersensing and may respond by increasing the sensitivity. For example, if marginal sensing is detected at a sensitivity of 4 mV, the IMD may increase sensitivity to 3 mV. Following the adjustment, the IMD may continue to monitor for a one-to-one relationship between electrical events and for marginal sensing.

One or more components of the IMD, such as the microprocessor, may execute and perform the processes and methods of the invention using algorithms stored in the memory. A variety of processes and methods may be performed by the IMD. In some embodiments, the appropriateness of a sensitivity level is monitored on an ambulatory basis by the IMD by continuously monitoring and analyzing electrical events and pressure waves. An example of such an embodiment is shown in the flow chart in FIG. 4. The process begins at the start 400, which may be implantation of the IMD, after which the IMD continuously cycles through the process. Alternatively, the IMD may be triggered to start the process by the microprocessor, such as at certain timing intervals which may be set by the manufacturer or by a physician. The IMD monitors electrical events and pressure waves and analyzes them for a one-to-one correlation 402 by looking for an association within a time window or by monitoring the ratio of the electrical event interval to pressure wave interval, as described above. If there is no approximately one-to-one correlation, a sensitivity adjustment is required.

Figure 4:
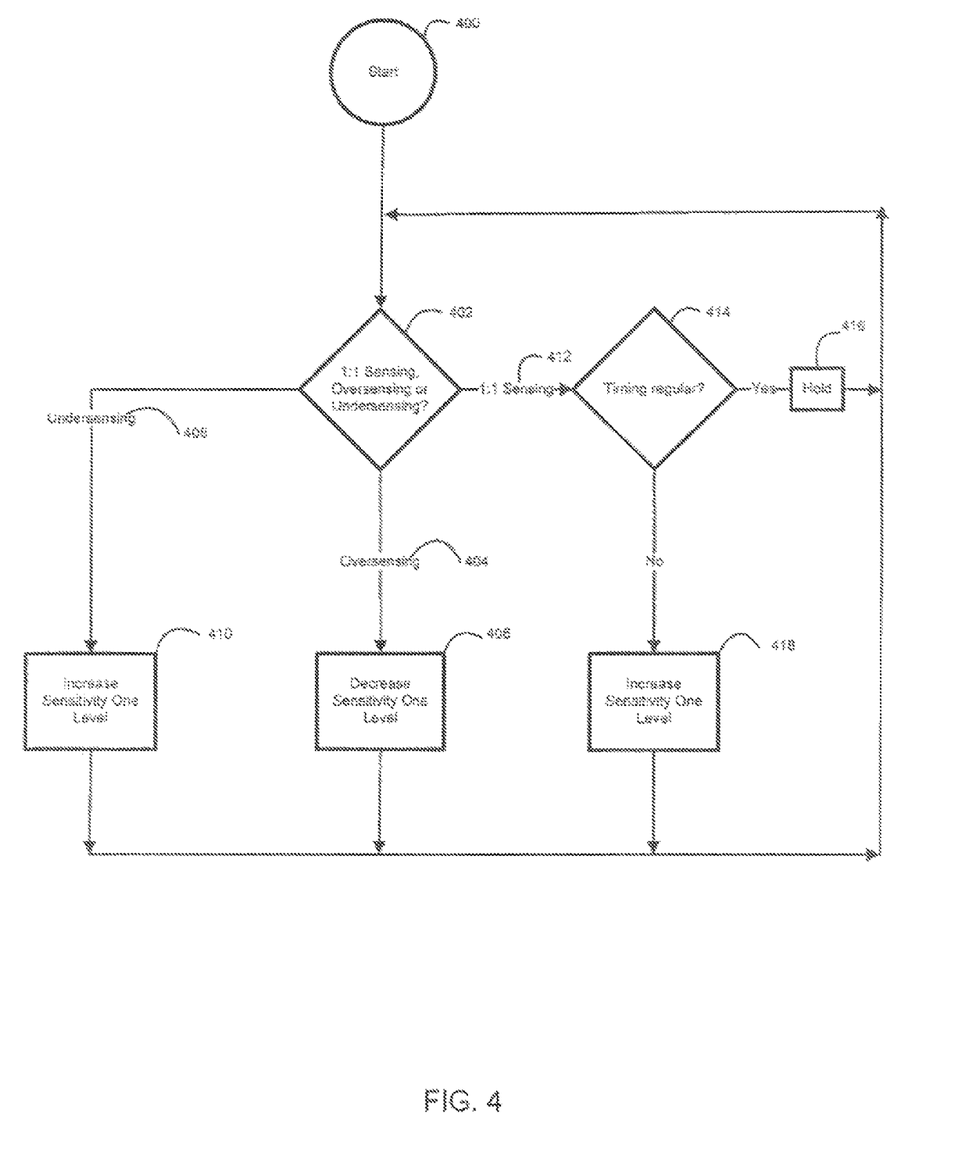
FIG. 4 is a flow chart of an ambulatory method of optimizing sensitivity using EGM and pressure data.

If the IMD detects an electrical event with no corresponding pressure wave, or the number of unassociated electrical events exceeds a maximum, the IMD determines that it is oversensing electrical events 404. To correct the oversensing, the IMD decreases the sensitivity one level 406. One level may be, for example, 0.5 mV or 1.0 mV, although any increment of adjustment could be used. Alternatively, if the IMD detects a pressure wave with no corresponding electrical event, or if the number of unassociated pressure waves exceeds a maximum, the IMD determines that it is undersensing 408. To correct the undersensing, the IMD responds by increasing the sensitivity one level 410. After increasing or decreasing the sensitivity, the IMD again compares electrical events and pressure waves to detect a one-to-one correlation, oversensing or undersensing 402. The IMD cycles through this process until a sensitivity level is found at which there is a one-to-one correlation between the electrical events and pressure waves 412.

When the IMD detects a one-to-one correlation between electrical events and pressure waves 412, the IMD determines there is no undersensing or oversensing and proceeds to assess whether the sensitivity level is adequate or marginal by determining whether the timing is regular 414. As described above, the IMD may assess the regularity of the timing of detected events by analyzing the interval between electrical events and pressure waves from beat to beat to detect a marginal sensitivity level. Alternatively, it may analyze the ratio of the interval between consecutive electrical events to the interval between consecutive pressure waves. If the timing is regular, the IMD determines that the sensitivity level is adequate and no adjustment is made 416. However, if the timing is not sufficiently regular, the IMD may determine that the sensitivity is marginally low and may therefore increase the sensitivity one level 418. After increasing the sensitivity, the IMD cycles back to check again for the continued presence of a one-to-one correlation between electrical events and pressure waves 402. Once a satisfactory sensitivity is identified, the process may then end or may restart. In some embodiments, the process may end and restart later, such as after a certain period of time or at a particular frequency.

Figure 5:
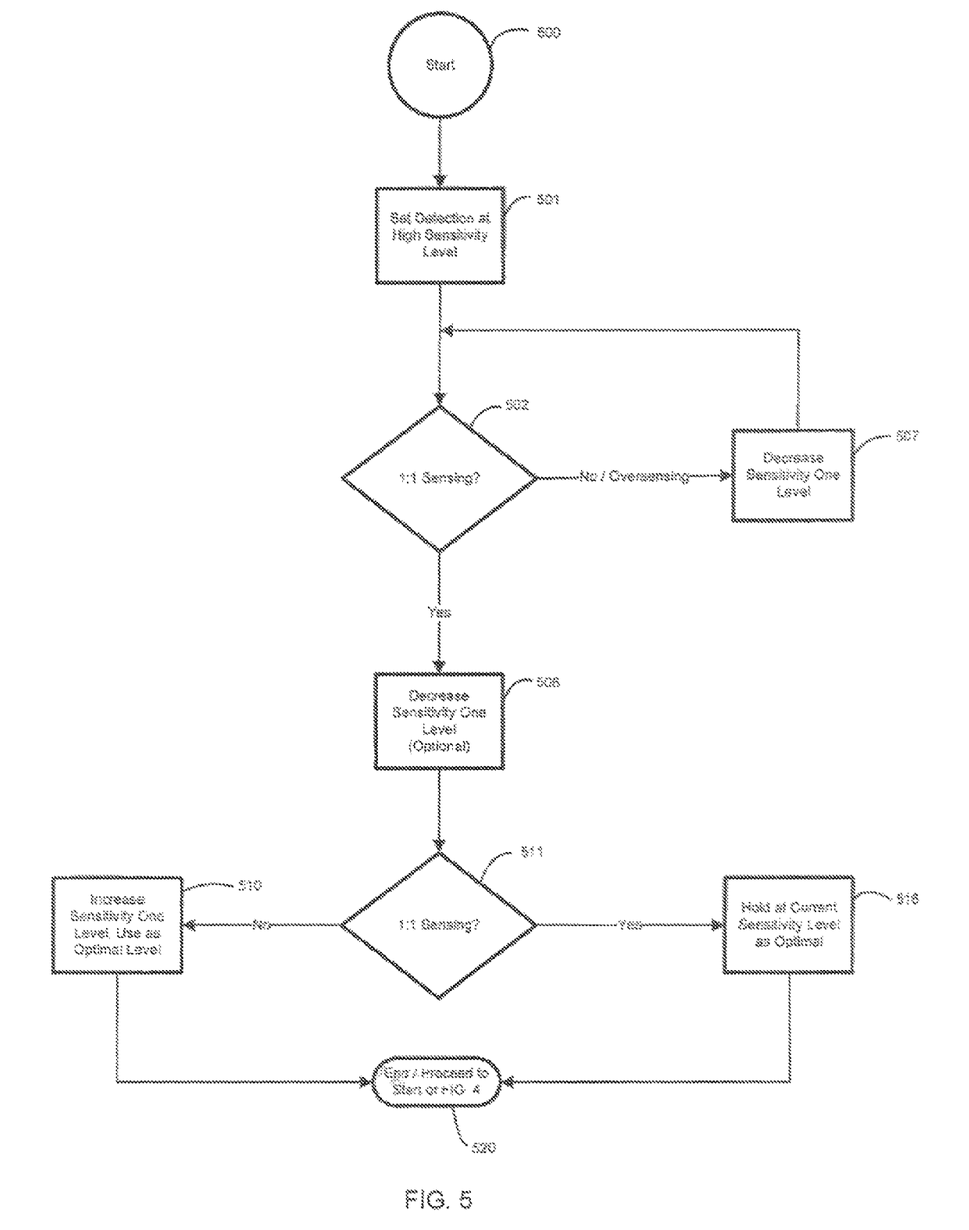
FIG. 5 is a flow chart of a method of optimizing sensitivity using EGM and pressure data.
Figure 6:
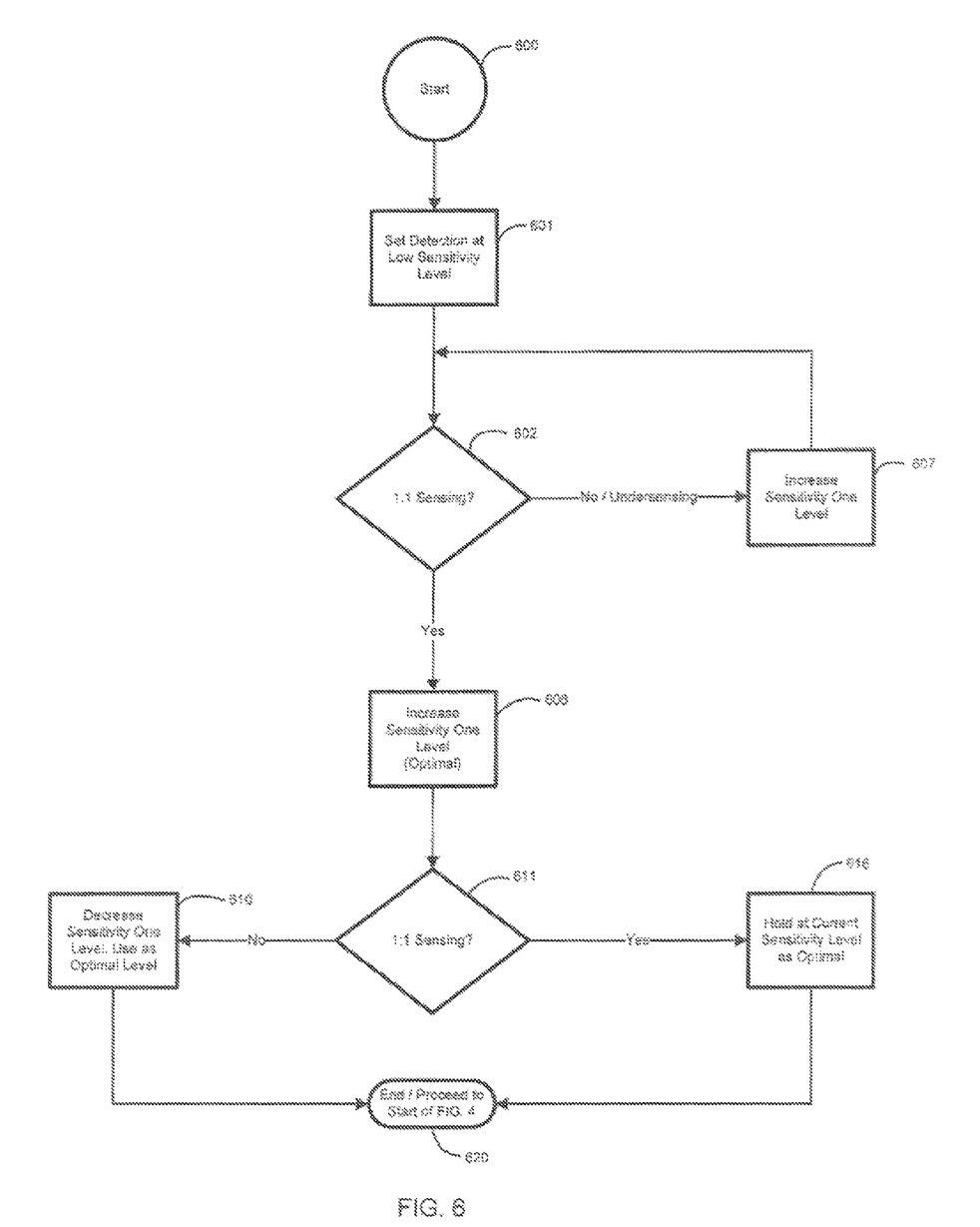
FIG. 6 is a flow chart of another method of optimizing sensitivity using EGM and pressure data.

FIGS. 5 and 6 are flow charts which demonstrate methods of determining an optimal sensitivity level according to embodiments of the invention. The start of optimization 500 may be implantation of the IMD. Alternatively, optimization according to these embodiments may be conducted on a periodic basis or may be triggered. For example, if the ambulatory process of FIG. 4 does not result in a satisfactory sensitivity level, such as after a certain number of cycles, the IMD may proceed with an optimization process according to FIG. 5 or 6.

In FIG. 5, optimization begins by setting the sensitivity of the IMD at a high level 501. For example, sensitivity could be set at 2 mV for ventricular detection. The IMD then monitors for a one-to-one correlation between electrical events and pressure waves 502, as described above, to derrermine if there is a one-to-one correlation, oversensing, or undersensing. If there is a one-to-one correlation between electrical events and pressure waves, the IMD then optionally decreases the sensitivity one level 506. By decreasing the sensitivity one level, a safety margin may be provided where possible. The IMD again monitors for a one-to-one correlation between electrical events and pressure waves 511. If present the IMD resets the sensitivity to this new level 516. However, if oversensing is detected at this level, the IMD increases the sensitivity one level 510 and sets the sensitivity to this level as optimal. If the IMD detects oversensing at the initial sensitivity level, the sensitivity is decreased one level 507 and the IMD again monitors the electrical events and pressure waves for one-to-one correlation 502. The IMD continues to decrease sensitivity one level at a time until consistent sensing is detected. The IMD then optionally decreases sensitivity one more level 506 and rechecks for a one-to-one correlation between electrical events and pressure waves 511. If the one-to-one relationship is present, this sensitivity level is set as optimal 516 and the optimization process ends at 520. However, if the IMD detects oversensing, the sensitivity is increased back up one level 510 and the level is set as optimal.

FIG. 6 demonstrates a process similar to that of FIG. 5, with the start of optimization at 600, but beginning at a low sensitivity level 601 such as 8 mV for ventricular detection. The sensitivity is increased stepwise 607 until there is a one-to-one relationship between electrical events, and pressure waves 602 indicating that there is no undersensing. Once an adequate sensitivity level is reached, the sensitivity is optionally increased one step further 606 to proVide a margin of safety. If oversensing is detected at 611, the sensitivity is decreased back to the previously identified adequate level 610 and the optimization process ends at 620. However, if no oversensing is detected, this level is selected as optimal 616. It is understood that methods of the present invention are not limited to those provided in FIG. 4-6. Other processes, such as iterative or binary search processes for determining and setting optimal sensitivity could be substituted or added to the methods described.

The invention claimed is:

1. A method of adjusting an electrogram (EGM) sensitivity level in an implantable medical device, comprising:
    using the device to monitor an EGM to detect electrical events at a sensitivity level;
    using the device to monitor intracardiac pressure to detect pressure waves; and
    using the device to analyze the detected electrical events and pressure waves to determine the presence or absence of a one-to-one correlation between detected electrical events and pressure waves, the absence of the one-to-one correlation indicating the need to adjust the sensitivity level, wherein the analyzing of the electrical events and pressure waves to identify the presence or absence of the one-to-one correlation comprises:
    before each detected pressure wave, determining whether there is an associated electrical event within a second time window, and
    wherein the one-to-one relationship is deemed present when the number of pressure waves without associated electrical events within the second time window measured over a predetermined number of pressure waves is less than a predetermined limit; and
    adjusting the sensitivity level in the absence of the one-to-one correlation.

2. A method according to claim 1, wherein monitoring intracardiac pressure to detect pressure waves comprises detecting dP/dt max.

3. A method according to claim 1, wherein undersensing is indicated when the one-to-one relationship is deemed absent.

4. A method of optimizing an electrogram (EGM) sensitivity level in an implantable medical device, comprising:
    a) detecting electrical events at a sensitivity level by monitoring an EGM;
    b) detecting pressure waves by monitoring an intracardiac pressure;
    c) analyzing corresponding electrical events and pressure waves to identify the presence or absence of a one-to-one correlation between detected electrical events and detected pressure waves;
    d) adjusting the sensitivity by one level in the absence of the one-to-one correlation until the presence of the one-to-one correlation is detected;
    e) setting the sensitivity level as the optimal level when the presence of the one-to-one correlation is detected; and
    f) at the optimal sensitivity level, monitoring the timing of detection of events from beat to beat to determine whether the sensitivity level is marginal.

5. A method according to claim 4, wherein monitoring the timing of detection of events from beat to beat to determine whether the sensitivity level is marginal comprises:
    timing an interval between a first electrical event and a first pressure wave as a first interval;
    timing an interval between a second electrical event and a second pressure wave as a second interval; and
    comparing the first and second intervals,
    wherein a difference between the first and second intervals of greater than a predetermined amount indicates that the sensitivity level is marginal.

6. A method according to claim 4, further comprising increasing the sensitivity one level when marginal sensitivity is detected.

7. A method according to claim 4, wherein adjusting the sensitivity by one level in the absence of the one-to-one correlation is performed repeatedly until the presence of the one-to-one correlation is detected.

8. A method according to claim 4, further comprising initially setting the sensitivity level at a low level and wherein adjusting the sensitivity level by one level in the absence of the one-to-one correlation involves an increasing the sensitivity level.

9. A method according to claim 4, further comprising initially setting the sensitivity level at a high level and wherein adjusting the sensitivity level by one level in the absence of the one-to-one correlation involves an decreasing the sensitivity level.

10. A method according to claim 4, further comprising adjusting the sensitivity level by one level past the optimal level at which the presence of the one to correlation was detected to determine whether the presence of the one-to-one correlation remains present.

* * * * *